(12) United States Patent
Daly et al.

(10) Patent No.: US 11,583,328 B2
(45) Date of Patent: Feb. 21, 2023

(54) FEMORAL NAIL AND INSTRUMENTATION SYSTEM

(71) Applicant: ORTHOXEL DAC, Bishopstown (IE)

(72) Inventors: Charles Daly, Kanturk (IE); Gerard Kiely, Carrigaline (IE); Micheal Keane, Tubber (IE); Sean O'Callaghan, Kanturk (IE); James Harty, Ovens (IE)

(73) Assignee: ORTHOXEL DAC, Bishopstown (IE)

( * ) Notice: Subject to any disclaimer, the term of this patent is extended or adjusted under 35 U.S.C. 154(b) by 0 days.

(21) Appl. No.: 17/278,088

(22) PCT Filed: Sep. 20, 2019

(86) PCT No.: PCT/EP2019/075410
§ 371 (c)(1),
(2) Date: Mar. 19, 2021

(87) PCT Pub. No.: WO2020/058508
PCT Pub. Date: Mar. 26, 2020

(65) Prior Publication Data
US 2021/0346075 A1   Nov. 11, 2021

(30) Foreign Application Priority Data
Sep. 21, 2018 (EP) .................................... 18196003

(51) Int. Cl.
*A61B 17/72* (2006.01)
*A61B 17/88* (2006.01)
*A61B 17/74* (2006.01)

(52) U.S. Cl.
CPC ...... *A61B 17/8872* (2013.01); *A61B 17/7241* (2013.01); *A61B 17/744* (2013.01)

(58) Field of Classification Search
CPC .............. A61B 17/7241; A61B 17/744; A61B 17/8872; A61B 17/1725
(Continued)

(56) References Cited

U.S. PATENT DOCUMENTS

| 7,410,488 B2 * | 8/2008 | Janna | A61B 17/725 |
| | | | 606/62 |
| 7,763,021 B2 * | 7/2010 | Cole | A61B 17/72 |
| | | | 606/64 |

(Continued)

FOREIGN PATENT DOCUMENTS

| EP | 1415605 A1 | 5/2004 |
| EP | 1779795 A1 | 5/2007 |

(Continued)

OTHER PUBLICATIONS

International Search Report and Written Opinion in corresponding Application No. PCT/EP2019/075410, dated Apr. 3, 2020, (19 pages).

*Primary Examiner* — Eduardo C Robert
*Assistant Examiner* — David C Comstock
(74) *Attorney, Agent, or Firm* — Bookoff McAndrews, PLLC

(57) ABSTRACT

An instrumentation system (100) and an intramedullary femoral nail system (1) for antegrade or retrograde implantation with laterally inserted bone screws, the system comprising a nail stem (2) having a multi-featured proximal end (3), a distal end and a central conduit (22) configured to accommodate a fastener (4), wherein the multi-featured proximal end (3) comprises a plurality of holes (20) configured to accommodate at least two bone screws (50, 52), wherein the first bone screw (50) is at an angle that is horizontal relative to the central conduit (22) and is on a coronal plane, and the second bone screw (52) is at an angle of between 120° to 130° relative to the central conduit (22).

20 Claims, 6 Drawing Sheets

(58) Field of Classification Search
USPC .............................. 606/62–65, 304, 308, 98
See application file for complete search history.

(56) References Cited

U.S. PATENT DOCUMENTS

| | | | | |
|---|---|---|---|---|
| 8,241,286 B2* | 8/2012 | Metzinger | ............... | A61B 17/72 606/86 R |
| 2002/0183750 A1 | 12/2002 | Buhler | | |
| 2003/0069581 A1* | 4/2003 | Stinson | ................. | A61B 17/72 606/62 |
| 2005/0101958 A1* | 5/2005 | Adam | .................... | A61B 17/72 606/62 |
| 2010/0152740 A1* | 6/2010 | O'Reilly | ............... | A61B 17/17 606/104 |
| 2012/0022533 A1* | 1/2012 | Buettler | ............. | A61B 17/1725 606/62 |
| 2012/0109127 A1* | 5/2012 | Overes | ................. | A61L 27/306 606/64 |
| 2012/0209268 A1 | 8/2012 | Overes | | |
| 2013/0116693 A1 | 5/2013 | Nelson et al. | | |
| 2014/0074093 A9 | 3/2014 | Nelson et al. | | |
| 2014/0214045 A1* | 7/2014 | Felder | ................... | A61B 17/72 606/104 |
| 2019/0314065 A1* | 10/2019 | Petersik | ................ | A61B 17/74 |
| 2019/0343569 A1* | 11/2019 | Hedgeland | ........... | A61B 17/744 |
| 2020/0113609 A1* | 4/2020 | Aneja | ................. | A61B 17/744 |

FOREIGN PATENT DOCUMENTS

| | | |
|---|---|---|
| WO | 2011018778 A1 | 2/2011 |
| WO | 2013120034 A1 | 8/2013 |
| WO | 2017178354 A1 | 10/2017 |

\* cited by examiner (A)

(B)

FEMORAL NAIL AND INSTRUMENTATION SYSTEM

CROSS-REFERENCE TO RELATED APPLICATION(S)

This patent application is a 371 National Phase of and claims the benefit of priority to Application No. PCT/EP2019/075410, filed on Sep. 20, 2019, which claims priority to EP Application No. 18196003.0, filed Sep. 21, 2018.

FIELD OF THE INVENTION

The invention relates to an intramedullary nail and instrumentation systems. In particular, the invention relates to a femoral nail that also includes a fastener with an alignment pin, a locking screw(s) and an endcap; and a system that includes the femoral nail and an instrumentation system for implanting the nail.

BACKGROUND TO THE INVENTION

Fractures of the femur are among the most serious long bone fractures, due to their potential for non-union, mal-union, and long-term dysfunction, as well as their propensity for open injury. Intramedullary nails have been in use for some time as aids in healing bone fractures and are the gold standard treatment option for such fractures. Intramedullary nailing acts as an internal splint and permits early weight bearing along with fracture healing.

WO 2011/018778 describes an intramedullary nail comprising a first part (an insert) having a first opening to receive a first fixture for engagement with a first bone fragment; a second part (a nail stem) having a second opening to receive a second fixture for engagement with a second bone fragment; and a motion assembly (a spring) which allows limited axial relative movement of the inset and nail stem. The insert is constrained to move axially only within the nail stem.

WO 2017/178354 describes an intramedullary nail system comprising a nail stem having a multi-featured proximal end, a distal end and a central conduit configured to accommodate a fastener having a proximal end, a distal end and a central shaft, wherein the fastener comprises a stop extending laterally from the proximal end relative to a vertical axis of the fastener and which is configured to matingly engage with an internal wall of the multi-featured proximal end to provide control over rotational and distal movement of the system when secured with a bone screw.

US 2013/0116693 describes a straight intramedullary bone fraction fixation device comprising an elongate body with a longitudinal axis and having both a flexible and rigid state and a compression screw. The device has a driver engaged with a feature on the distal end of the nail to raise a feature on the outer surface of the nail to secure the nail to the bone. It achieves this by axially translating a member that runs through the central portion whose distal tip has a substantially circular feature. When the member is rotated it moves in a proximal and axial direction that pushes out the securement feature.

US 2002/0183750 describes a femur nail for insertion between the condylii of the knee joint. The nail comprises at least two fastening bores that cross the longitudinal axis of an end piece of the nail. This nail is for retrograde insertion only and the screw trajectories are not suitable for antegrade insertion.

The problems with intramedullary nails currently being used is that screw fixation is not optimised to treat the various type of fractures and clinical modalities presented from various patients. Further, the instrumentation devices currently being used do not deliver the intramedullary nails accurately and safely to ensure that the fixation is optimised to treat various type of fractures and clinical modalities. In addition, the following clinical effects are routinely seen from the implanted devices:
Unequal load spread over the femur particularly in the neck of femur to device;
Inability to compress neck of femur fractures;
Screws backing out from placed location;
Screws cutting out from the bone in the femoral head;
Multiple nail sizes required to treat antegrade vs. retrograde device insertion with the addition of many instrumentation steps and specific instruments.

It is an object of the present invention to overcome at least some of the above-mentioned problems.

SUMMARY OF THE INVENTION

The inventors have developed a new femoral nail and instrumentation system for implantation from an antegrade (hip) or retrograde (knee) direction that also includes a fastener with alignment pin, laterally inserted locking screws and endcaps.

According to the present invention there is provided, as set out in the appended claims, an intramedullary nail system for antegrade or retrograde implantation with laterally inserted bone screws, the system comprising a nail stem having a multi-featured proximal end, a distal end and a central conduit configured to accommodate a fastener, wherein the multi-featured proximal end comprises a plurality of holes configured to accommodate at least two laterally inserted bone screws, wherein the first bone screw is at an angle that is horizontal relative to the central conduit and is on a coronal plane, and the second bone screw is at an angle of between 120° to 130° relative to the central conduit.

According to the present invention there is provided, as set out in the appended claims, an intramedullary femoral nail system for antegrade or retrograde implantation with laterally inserted bone screws, the system comprising a nail stem having a multi-featured proximal end, a distal end and a central conduit; and a fastener, wherein the central conduit is configured to accommodate the fastener, wherein the fastener comprises a raised foot at a proximal end thereof; wherein the multi-featured proximal end comprises a plurality of holes configured to accommodate at least three laterally inserted bone screws wherein the first hole configured to accommodate the first bone screw is at an angle that is horizontal relative to the central conduit and is on a coronal plane, the hole configured to accommodate the second bone screw is at an angle of between 120° to 130° relative to the central conduit, and the hole configured to accommodate the third bone screw is at an angle of 124.5° relative to the central conduit, and wherein the second and third bone screws accommodated within the holes are not parallel to each other.

In one aspect, the angle can be 120°, 120.5°, 121°, 121.5°, 122°, 122.5°, 123°, 123.5°, 124°, 124.5°, 125°, 125.5°, 126°, 126.5°, 127°, 127.5°, 128°, 128.5°, 129°, 129.5°, or 130° relative to the central conduit.

In one embodiment, the second bone screw is at an angle of 128° relative to the central conduit and in an ascending approach relative to the first bone screw. In one embodiment, the third bone screw is at an angle of 128° relative to the central conduit and in a descending approach relative to the first bone screw.

The intramedullary femoral nail system for antegrade or retrograde implantation further comprises a fourth laterally inserted bone screw, wherein the fourth bone screw is an at an angle of 124.5° relative to the central conduit. Preferably, the second and fourth bone screws are rotated at an angle of 14° in an anterior direction relative to the coronal plane.

In one embodiment, the third bone screw is an at an angle of 128° relative to the central conduit and in a descending approach relative to the first bone screw and second screw. Preferably, the third bone screw is rotated at an angle of 14° in a posterior direction relative to the coronal plane.

The intramedullary femoral nail system further comprises an end cap adapted to matingly engage with a threaded portion of the proximal end of the nail stem. Preferably, rotational movement of the endcap advances the fastener distally against one or more proximally placed bone screws and rigidly locks the nail system to prevent axial and torsional motion.

The intramedullary femoral nail system further comprises an alignment pin adapted for securing the fastener within the nail stem during transport and use.

The intramedullary femoral nail system further comprises a medio lateral fifth bone screw that can be placed distal to all other bone screws (50,52,54,56).

There is also provided, as set out in the appended claims, an instrumentation system for use with the intramedullary femoral nail system described above, wherein the instrumentation system comprises an aiming arm, a connecting bolt configured to matingly engage with the nail stem and a fastener camlock configured to matingly engage with the fastener.

There is also provided, as set out in the appended claims, an instrumentation system for use with the intramedullary femoral nail system described herein for antegrade or retrograde implantation with laterally inserted bone screws, wherein the instrumentation system comprises an aiming arm, a cannulated connecting bolt comprising a threaded portion that is configured to matingly engage with a nail stem of the nail system, a fastener comprising a raised foot at a proximal end thereof configured to engage with the nail system, and a fastener camlock comprising an end cam feature configured to matingly engage with the fastener and the cannulated connection bolt.

In one embodiment, the fastener camlock comprises a cam feature end, a shaft section, and a distal head. The shaft section engages the cannulated connecting bolt. In one embodiment, the fastener camlock cam feature end is substantially non-circular. Preferably, the cam feature end is configured to engage with a raised foot at the proximal end of the fastener. Preferably, the raised foot further comprises a berm that is configured to matingly engage with the cam feature end via radial force against the fastener. Preferably, the rotational movement of the fastener camlock presses against the fastener which is held by the alignment pin in the axial position.

In one embodiment, when the alignment pin is removed, the fastener is held in position.

The instrumentation system for use with the intramedullary femoral nail system described above further comprises a modular block configured to attach to the aiming arm. The modular block consistently provides lateral bone screw trajectories for either a right or a left antegrade or retrograde implantation. Ideally, when the modular block is attached to the aiming arm via pins on the aiming arm, the modular block presents the bone screw trajectories for inserting the bone screws. Preferably, the pins on the aiming arm further comprise wings which block any redundant screw trajectories when the modular block is attached to the aiming arm.

In one aspect, the nail stem for use in conjunction with the instrumentation system comprises a nail stem having a multi-featured proximal end, a distal end and a central conduit; and a fastener, wherein the central conduit is configured to accommodate the fastener, wherein the fastener comprises a raised foot at a proximal end thereof; wherein the multi-featured proximal end comprises a plurality of holes configured to accommodate at least three laterally inserted bone screws wherein the first hole configured to accommodate the first bone screw is at an angle that is horizontal relative to the central conduit and is on a coronal plane, the hole configured to accommodate the second bone screw is at an angle of between 120° to 130° relative to the central conduit, and the hole configured to accommodate the third bone screw is at an angle of 124.5° relative to the central conduit, and wherein the second and third bone screws accommodated within the holes are not parallel to each other.

There is also provided an instrumentation system and an intramedullary femoral nail system for antegrade or retrograde implantation with laterally inserted bone screws, wherein the instrumentation system comprises an aiming arm, a cannulated connecting bolt comprising a threaded portion that is configured to matingly engage with a nail stem of the nail system, a fastener comprising a raised foot at a proximal end thereof configured to engage with the nail system, and a fastener camlock comprising an end cam feature configured to matingly engage with the fastener; wherein the intramedullary femoral nail system comprises a nail stem having a multi-featured proximal end, a distal end and a central conduit configured to accommodate the fastener, and the fastener, wherein the multi-featured proximal end comprises a plurality of holes configured to accommodate at least three laterally inserted bone screws, wherein the first hole configured to accommodate the first bone screw is at an angle that is horizontal relative to the central conduit and is on a coronal plane, the hole configured to accommodate the second bone screw is at an angle of between 120° to 130° relative to the central conduit, and the hole configured to accommodate the third bone screw is at an angle of 124.5° relative to the central conduit, and wherein the second and third bone screws accommodated within the holes are not parallel to each other.

There is also provided, as set out in the appended claims, a kit of parts for use in repairing a bone fracture, the kit comprising an intramedullary femoral nail system and the instrumentation system as described above.

The kit further comprises an alignment pin. The kit further comprises a connecting bolt and a fastener camlock. The kit further comprises a locking end cap and/or a non-locking end cap.

In one embodiment, the material of construction of the nail system and the instrumentation system is suitably a durable, rigid and biocompatible material, for example, implant-grade titanium alloys (such as titanium-aluminium-vanadium (Ti-6AL-4V EL164) or titanium-aluminium-niobium (Ti-6Al-7Nb)), stainless steel (316L or 316LVM), or any other metal alloy, composite, polymer material or combination thereof that is suitable for load-bearing application as an in vivo implant.

One aspect of the invention is an intramedullary nail system as described herein for use in a method for repairing a bone fracture, the method comprising the steps of:

Positioning the affected limb of the patient;

Opening a portal to the medullary canal, at the proximal femur for antegrade or distal femur for retrograde, by separating the soft tissue and drilling a short entry passage;

Reaming the medullary canal if deemed appropriate by the surgeon;

Selecting the appropriate nail diameter and length from radiographic templating and taking reference to the last reamer size;

Attaching the surgical instruments to the nail with the fastener and alignment pin in place, such that the fastener becomes constrained from motion relative to the nail by the connecting bolt and fastener camlock;

Removing the alignment pin;

Inserting the nail into the medullary canal;

Confirming fracture alignment by radiographic means;

Drilling for and inserting distal bone screws of number and alignment chosen according to the surgeon's judgement using a free-hand technique;

Drilling for and inserting proximal bone screws of number and alignment chosen according to the surgeon's judgement and using the provided targeting instrumentation to achieve:

Micro-dynamisation locking mode,

Interlocked mode (ascending and descending screws), or

Recon-locked mode (ascending screws);

Removing the surgical instruments from the IM nail system;

Inserting an endcap according to the surgeon's judgement, either:

Standard endcap, or a Locking endcap to achieve a substantially rigid locking configuration; and Closing all soft tissue.

The advantages of the intramedullary nail described herein is that screw fixation is optimised to treat the various type of fractures and clinical modalities presented from various patients. The intramedullary nail includes the following features:

Ability to compress neck of femur fractures via proximal mediolateral screw;

Changing the screw loading in the femoral head to reduce the likelihood of screws cutting out from the bone in the femoral head;

Equal load spread over the femur proximally, due to the addition of a medio lateral screw through the greater trochanter-nail-femoral head to reduce the bending moment relative to having ascending screws only;

Reduce likelihood of screws backing out from placed location due to the clamping effect of the locking endcap on all screws;

One nail for antegrade vs. retrograde device insertion and right/left patient legs;

Simple intuitive aiming arm instrumentation that assembles to nail and only presents the surgeon with the desired screw placement locations;

After instrument assembly no alignment pin removal force, but effective holding of the fastener relative to the nail stem; and All bone screws are placed from the lateral side, due to ease of insertion away from clinical areas of concern, and the ascending bone screw moves generally from anterior to posterior and the descending bone screw from posterior to anterior.

Definitions

In the specification, the term "micro-dynamisation locking" should be understood to mean securing the IM nail system as described herein in position using bone screws and wherein positioning the bone screws in medio lateral openings (long dynamisation slot and aperture distal to long slot) of the nail stem and the corresponding fastener holes allows controlled axial low force movement of the proximal bone fragment with limited rotation while the IM nail system is secured in situ. In this configuration, the fastener can slide distally and proximally over approximately 0.01-2 mm, preferably 0.1-2 mm, more preferably 0.5-1.5 mm, ideally 0.75-1 mm, or greater than 1.5 mm but no more than 2 mm, and generally greater than 0.5 mm but no more than 1.5 mm, with this distance determined by the dimensions of the micro-dynamisation slot in the stem and of the bone screw that is placed in the aligned hole in the fastener.

In the specification, the term "interlocking configuration" should be understood to mean locking of the IM nail system described herein in position using bone screws, and where the positioning of the bone screws in the holes of the proximal end of the nail stem, and the fastener, is chosen such that at least two screws are oriented in different planes. When viewed along the frontal plane of the nail stem, the central axes of the cross-locked screws cross to form an "X"-type shape. This provides a semi rigid locking of the system dependent on the degree of dimensional variation between the bone screw and relevant hole.

In the specification, the term "recon configuration" should be understood to mean locking of the IM nail system described herein in position using bone screws, and where the positioning of the bone screws in the holes of the proximal end of the nail stem, and the fastener, is chosen such that at least one screw is oriented in an ascending direction towards the end of the nail. In practice two screws can be placed that are ascending and are relatively parallel. This provides a semi-rigid locking of the system dependent on the degree of dimensional variation between the bone screw and relevant hole.

In the specification, the term "a substantially rigid locking configuration" should be understood to mean a configuration of the IM nail system described herein, in which the nail is locked in position relative to the bone fragments using bone screws and endcaps, where the positioning of the bone screws in the multi-featured proximal end of the nail stem and the fastener is restricted by the endcap to allow very little or no relative movement of any component. In this configuration, significant movement of the bone fragments can only occur due to elastic flexure of the IM nail system components during active weight bearing applied by the patient.

In the specification, the term "multi-featured proximal end" should be understood to mean the proximal end of the nail stem having a suite of features. The suite of features consists of holes, apertures, longitudinal indentation or slots configured to accommodate bone screws, an alignment pin or fastener. The longitudinal indentation along the internal wall of the proximal end first provides clearance for a stop on the fastener to engage with a slot on the nail stem, and a further interfacing hole allows the stop to advance distally when the fastener is placed within the central conduit of the nail stem.

In the specification, the term "unstable proximal fracture patterns" should be understood to mean bone fractures occurring near the knee or hip joints that may be considered clinically suitable for fixation by IM nailing, but are not mechanically stable due to the orientation of the fracture line(s).

In the specification, the term "non-locking endcap" or "standard endcap" should be understood to mean an endcap which sits in the threads at the proximal end of the nail stem and does not engage with any other component. The endcap's purpose is to prevent bone ingrowth into the nail and sometimes to extend the nail length proximally by 5-15 mm, as is common practice in intramedullary nailing.

In the specification, the term "locking endcap" should be understood to mean an endcap which sits in the proximal threads of the nail stem and has the same function as the non-locking endcap, except that is also engages with the fastener. The locking endcap provides a distally directed force by means of the screw threads to compress any bone screw(s) carried by the fastener firmly into the distal face of each corresponding hole in the nail stem. This produces a substantially rigid construct.

In the specification, the term "cam feature end" should be understood to mean a feature on the end of the fastener camlock with a profile when inserted to the connecting bolt assembled with clearance and when rotated clockwise has a projection that makes sliding contact with another mating part. Where continuous rotation locks the profile against the mating part with increasing force to indicate to the user that the parts are relatively fixed. Anticlockwise rotation unlocks the parts relatively allowing for the fastener camlock withdrawal.

BRIEF DESCRIPTION OF THE DRAWINGS

The invention will be more clearly understood from the following description of an embodiment thereof, given by way of example only, with reference to the accompanying drawings, in which:—

FIGS. 1A and 1B illustrate the classical two bone screw recon locking mode that is widely used but with an additional new mediolateral bone screw (50) from the greater trochanter through the piriformis fossa and into the femoral head.

FIGS. 1C and 1D illustrates an additional locking mode which removes one ascending bone screw as shown in FIG. 1A/B and sets it as a descending bone screw which traverses from the greater to the lesser trochanter of the femur. FIGS. 1E and 1F illustrate a micro-dynamisation locking mode which secures the IM nail uniformly over the proximal end of the femur and allows up to 1 mm of motion of the fastener relative to the nail. In all these cases an additional bone screw can be added in the mediolateral direction which is distal on the femur to the shown screws.

FIGS. 2A and 2B illustrate interlocking bone screws in three planes that are also rotated anterior and posterior (off axis) relative to each other.

FIGS. 2C and 2D, and FIGS. 2E and 2F illustrates an arrangement similar to that of FIGS. 1E and 1F which allows micro-dynamisation locking which secures the nail uniformly over the femur and allows up to 1 mm of motion of the fastener relative to the nail. In all these cases an additional screw can be added in the mediolateral direction which is proximal on the femur to the shown screws.

FIG. 3A shows an exploded view of the IM nail, a fastener, an alignment pin, an aiming arm, a connecting bolt and a fastener camlock. FIG. 3B illustrates a sectional view of the IM nail system of FIG. 3A when assembled along axis A-A, while FIG. 3C illustrates a side view of the instrumentation connected to the nail system. FIG. 3D illustrates a closer view of section C from FIG. 3A.

FIG. 4B shows the cam when rotates engaging the cam feature on the raised foot on the proximal end of the fastener. This then radially clamps the fastener relative to the nail stem. Finally, the alignment pin is withdrawn with very little force (as the clamping mechanism is radial and not axial, no force has been applied during assembly/clamping). The nail and aiming arm are now ready for attachment of the blocks for screw targeting as shown in FIG. 5.

FIGS. 5A-5B show the instrumentation of the present invention for use with antegrade implantation of the right leg or retrograde insertion for the left leg. FIGS. 5C-5D, the instrumentation of the present invention for use with an antegrade implantation of the left leg or retrograde insertion for the right leg. In all cases, the aiming arm is attached to the nail and secured with the connecting bolt and fastener camlock, two further blocks are slid in laterally. The blocks are interchangeable for left (FIGS. 5A-5B) and right (FIGS. 5C-D) sides and left/right leg and can only be placed in one orientation. The advantage of these blocks is when they are slid on a wing blinds the surgeons to only those holes that are to be used for pilot hole drilling and locking bone screw insertion.

DETAILED DESCRIPTION OF THE DRAWINGS

Like all intramedullary nails, the intramedullary nail system described herein sits within the hollow space inside the bone. Screws placed above and below the fracture stabilise the bone fragments to allow healing. Small axial movements along the length of the bone help speed up healing, while twisting movements slow down healing. The nail described herein offers both controlled axial motion and very little twisting, providing the optimum healing conditions at the fracture site, reducing both the healing time and time to patient weight bearing.

In addition to controlled axial micro-motion and torsional stability, the nail system described herein offers screw trajectories that allow for securement of neck of femur fractures with three screws, rather than the conventional two screws, thus spreading the load on a wider area on the femoral head. This changes the conventional assessment of fixation, "tip apex distance" and reduces the likelihood of "cut out" of the screws through the femoral head. This new screw configuration simultaneously spreads the load on the femur lateral face over a larger area from just under the tip of the greater trochanter to the sub trochanteric region. Fractures that occur across the neck of the femur can also be compressed using the proximal medio lateral screw. In addition, through placing the locking endcap, there is a reduced likelihood of the bone screws backing out from their placed location due to the clamping effect of the locking endcap on all placed screws simultaneously.

Figure 1:
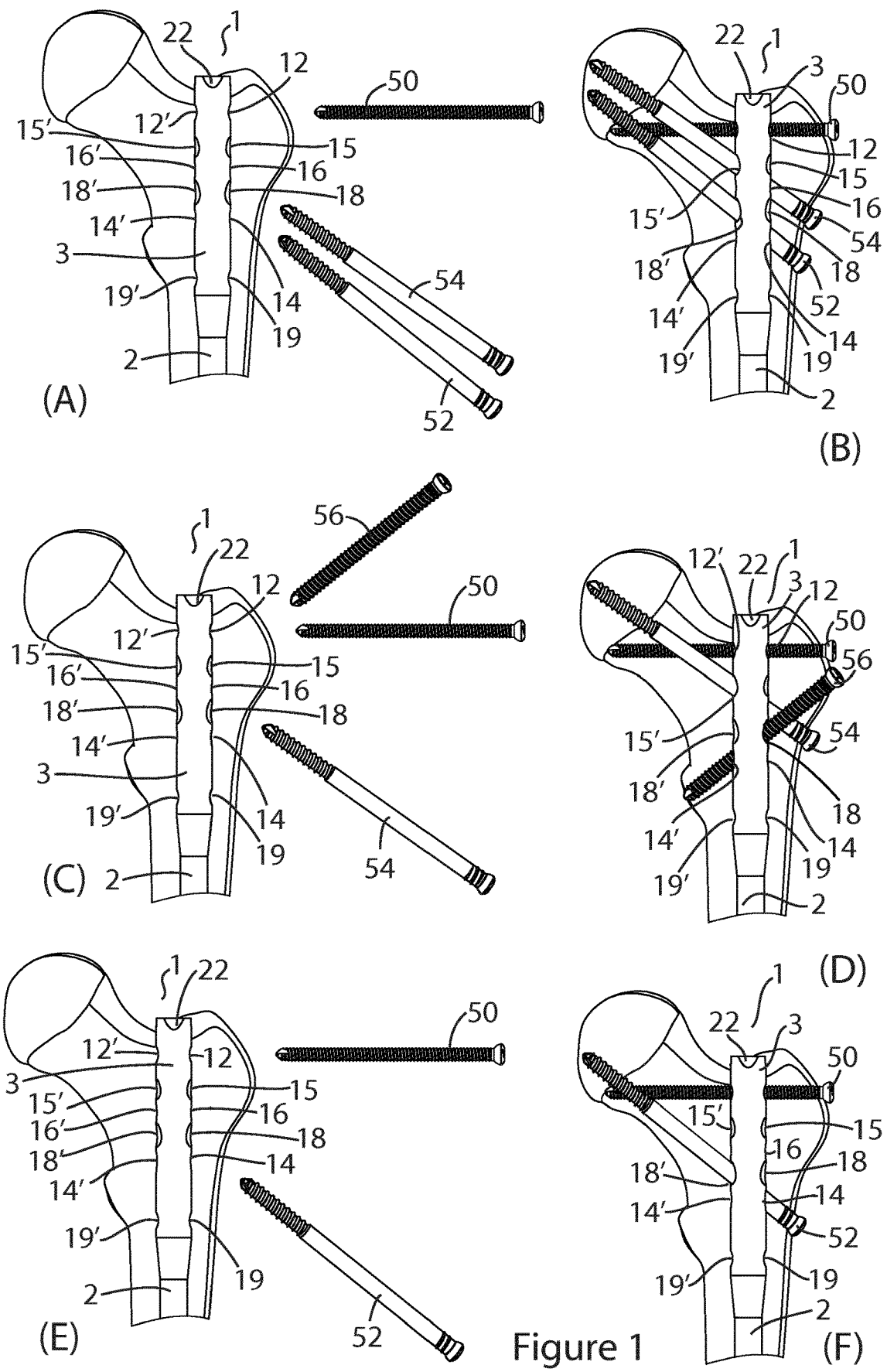
FIG. 1 illustrates three different antegrade (hip) nail implantation screw trajectory insertion options for the surgeon using an intramedullary (IM) femoral nail of the present invention.

Referring now to the figures, where FIG. 1 illustrates a general embodiment of an intramedullary (IM) nail of the present invention for antegrade (hip) insertion. Specifically, FIG. 1 illustrates three different antegrade insertion options for the surgeon using an IM nail system of the present invention and is generally referred to by reference numeral 1. The IM nail system 1 illustrated here comprises a nail stem 2 comprising a distal end and a multi-featured proximal end 3. The nail stem 2 is made from a single piece of material. The multi-featured proximal end 3 of the nail stem 2 comprises an aperture or hole 12, which lies proximal and oblique to hole 14,16 with the same line of symmetry and a conduit 22 through which a fastener (not shown, see FIG. 3 where it is assigned reference numeral 4). The aperture 14 can be either in the form of a slot (an elongated aperture 14') or a hole (a substantially circular aperture 14). The holes or slots found in either the nail stem 2 or the fastener 4 of the system 1 are defined by the internal dimensions of a cut-out section (hole or elongated slot) in the nail stem 2 and the fastener 4, respectively. The internal dimensions are generally defined by a circumference edge. The multi-featured proximal end 3 further comprises medial lateral holes 12,19 positioned oblique to holes 14,16,18. All of the holes are configured to accommodate a bone screw. Hole 12 accommodates bone screw 50. Hole 14,14' accommodate bone screw 52 for left-right leg, respectively. Hole 16,16' accommodate bone screw 54 for left-right leg, respectively. Hole 18,18' accommodate bone screw 56 for left-right leg, respectively. Hole 15 and 15' are clearance holes so no additional bone screw is placed though these. In practice, the function for hole 15,15' is for bone screw 54 to go through hole 16 and comes out through hole 15' or in through hole 16' and out through hole 15 for left vs right, respectively.

FIG. 1A/1B shows the classical two bone screws 52,54 recon ascending screw (the close to parallel screws at a substantially 124° angle relative to the nail axis and rotated approximately 14° anterior from the medio lateral plane) locking mode that is widely used, but with the addition of a new mediolateral bone screw 50 from the greater trochanter through the piriformis fossa and into the femoral head. A standard endcap can be placed with this configuration or locking endcap if clamping of all the screws is required. FIGS. 1C/D shows an additional interlocking mode with an interchange of the recon bone screw 52 for a descending bone screw 56 relative to nail axial and rotated posterior approximately 14°, which traverses from the greater to the lesser trochanter, the third medio lateral screw adding a further interlock. Interlocking places the bone screws 50,52, 54 in multiple planes, ascending rotated anterior, descending rotated posterior and medio lateral on axis, to improve load spread and bone fixation. FIG. 1E/F illustrates a micro-dynamisation locking mode which secures the nail 2 uniformly over the proximal end of the femur via the recon ascending bone screw 52 and medio lateral bone screw 50 and allows up to 1 mm of motion of the fastener 4 relative to the nail 2. The benefits of spreading the bone screw fixation points across the bone is that it provides a more uniform fixation from the femoral head to the greater trochanter and resulting axial movement (micro-dynamisation). This effectively optimises fixation stability while also adding in the desired micro-dynamisation.

Figure 2:
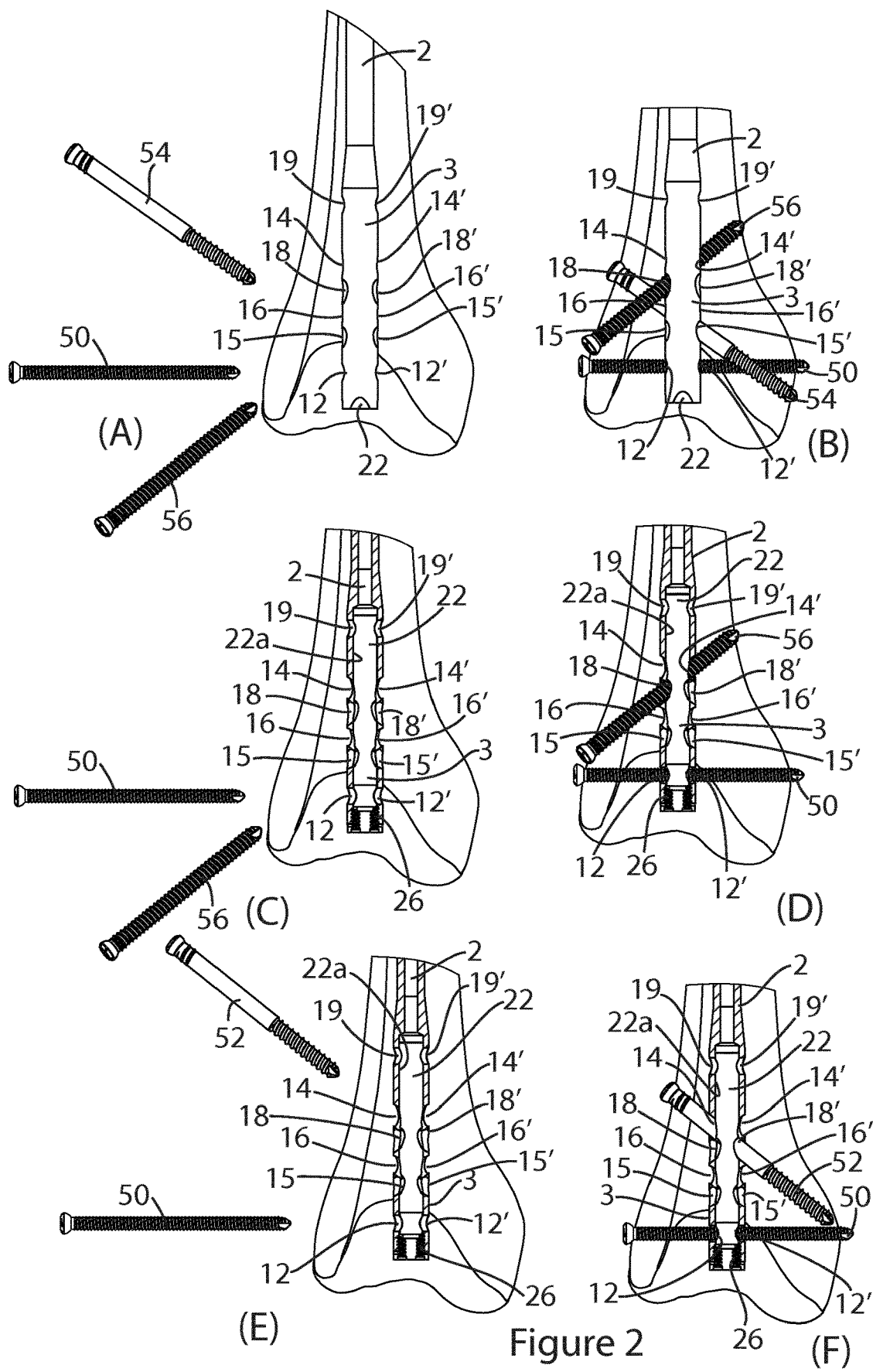
FIG. 2 illustrates three different retrograde (knee) nail implantation screw trajectory insertion options for the surgeon using an intramedullary (IM) nail of the present invention.

FIG. 2 illustrates a side view of the nail stem 2 for retrograde (knee) insertion. FIGS. 2A and 2B illustrate interlocking bone screws 50,52,56 in three planes that are also rotated anterior and posterior (off axis) relative to each other. FIGS. 2C-2F illustrates a micro-dynamisation locking mode which secures the nail 2 uniformly over the distal end of the femur via an ascending/descending screw 56/52 and medio lateral screw 50 and allows up to 1 mm of motion of the fastener 4 relative to the nail 2. The benefits of spreading the bone screw fixation points across the bone provide a more uniform fixation and tailoring for the specific fracture pattern. The multi-featured proximal end 3 illustrated in FIG. 2 is the same as that illustrated in FIG. 1. Specifically, that the proximal end 3 comprises medial lateral holes 12,19 positioned oblique to holes 14,16,18. Hole 12 accommodates bone screw 50. Hole 14,14' accommodate bone screw 52 for left-right leg, respectively. Hole 16,16' accommodate bone screw 54 for left-right leg, respectively. Hole 18,18' accommodate bone screw 56 for left-right leg, respectively.

Typically, bone screws 52,54,56 are angled in two planes so, for example, bone screw 52 enters hole 14 and exits hole 18'; bone screw 54 enters hole 16 and exits hole 15'; and bone screw 56 enters hole 18 and exits hole 14'. The horizontal bone screw 50 enters hole 12 and exits hole 12'.

What should be noted is that any of the above illustrated nail locking configurations can include a fourth bone screw added in the mediolateral direction which is distal on the nail 2 to the shown bone screws 50,52,54,56. Combined with the clamping effect on all four bone screws simultaneously through the use of a locking endcap that presses against the preloaded fastener in the proximal end 3 of the nail stem 2 and clamps all placed bone screws, very strong rigidity is provided to the locking mechanism.

Figure 3:
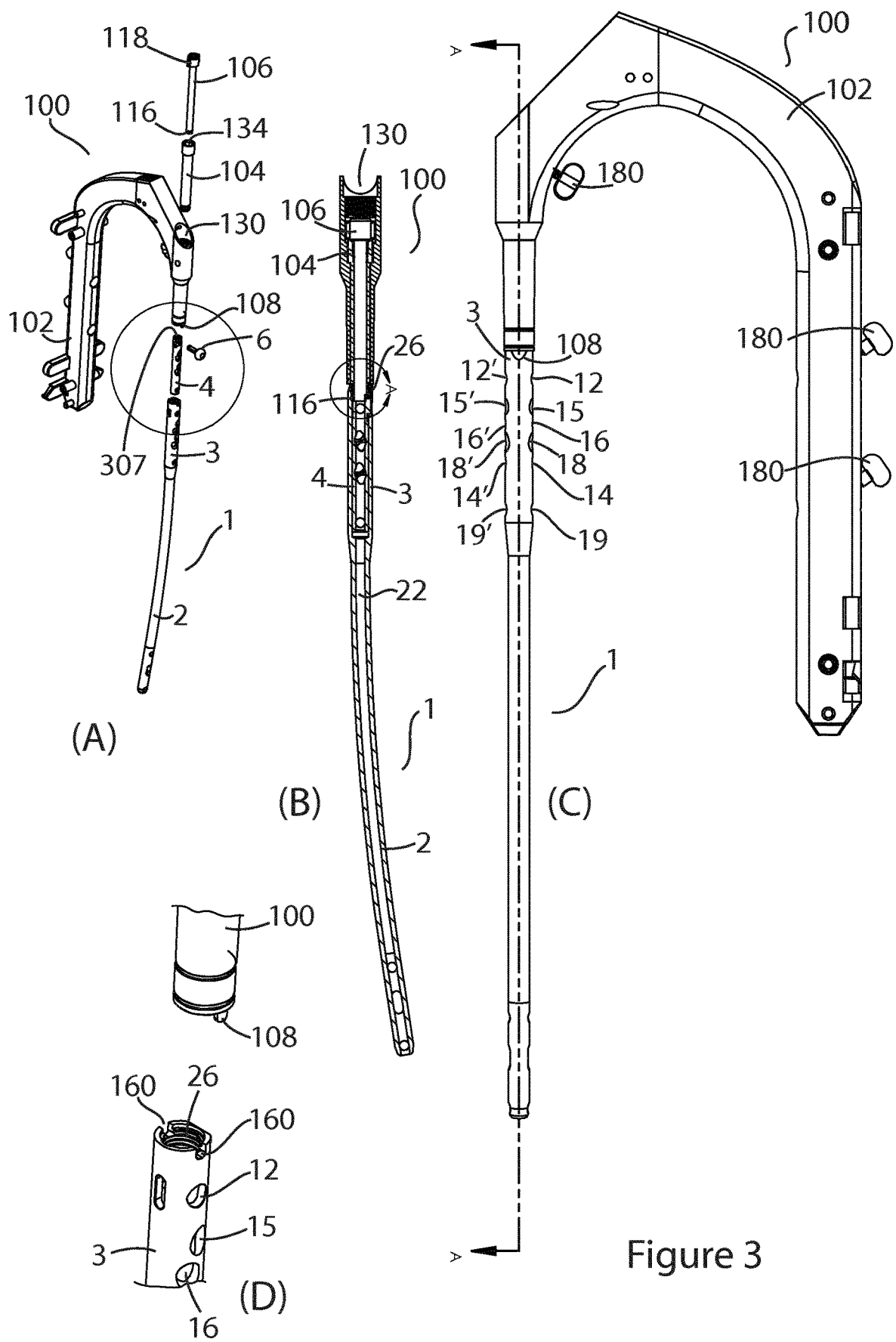
FIG. 3 illustrates exploded and sectional views of the IM nail system and instrumentation system of the present invention.
Figure 4:
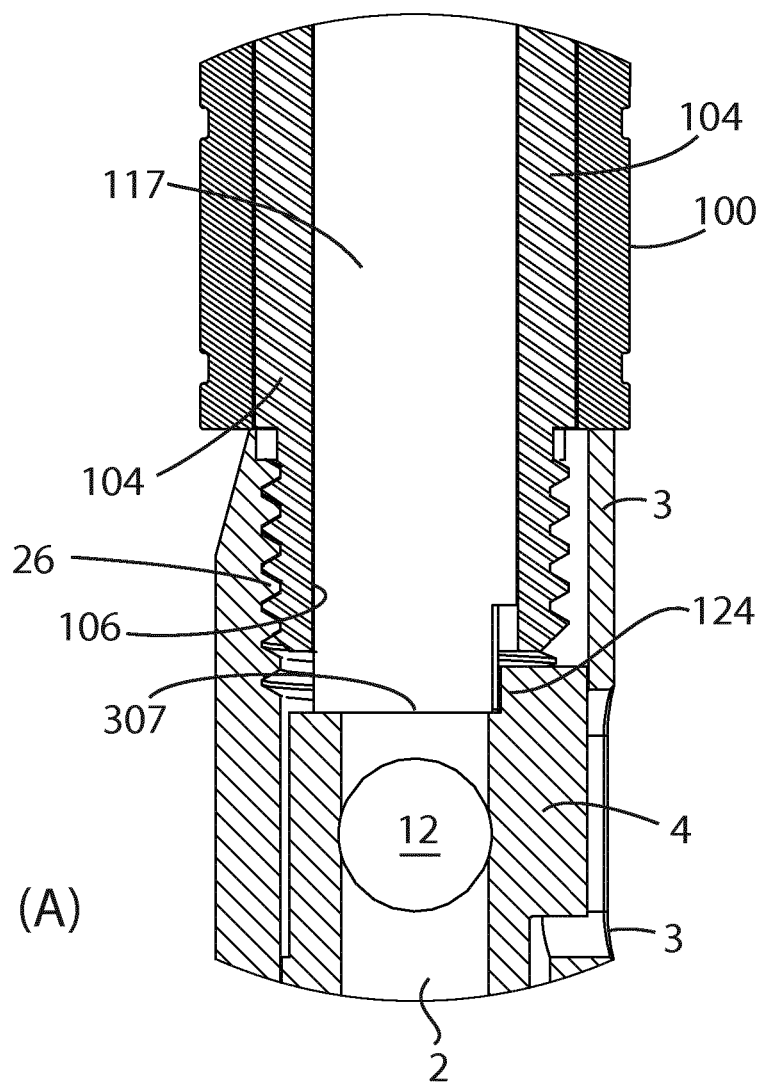
FIG. 4 illustrates view 'A' highlighted in FIG. 3B and shows in FIG. 4A an aiming arm with a raised tooth that presses into the end of the nail to provide rotation alignment, it is held in place by an insertion bolt that passes through the conduit on the aiming arm and threads into the proximal end of the nail, fixing the nail and aiming arm. The fastener camlock is inserted into the conduit of the connection bolt until it stops against the top surface of the fastener.
Figure 4:
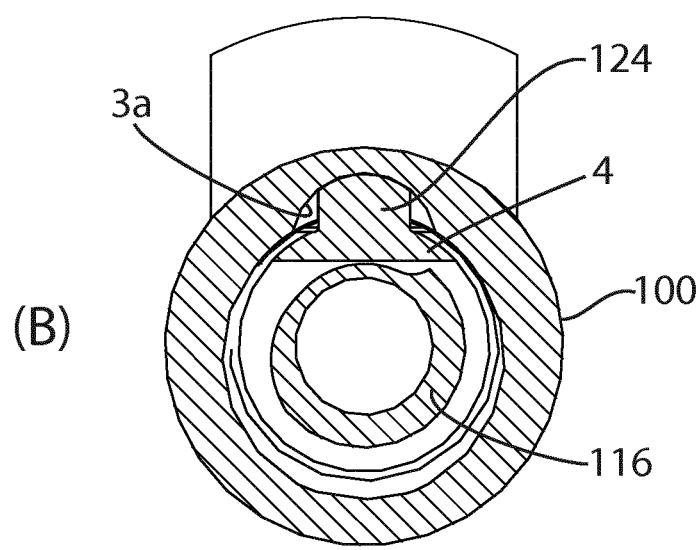
Figure 5:
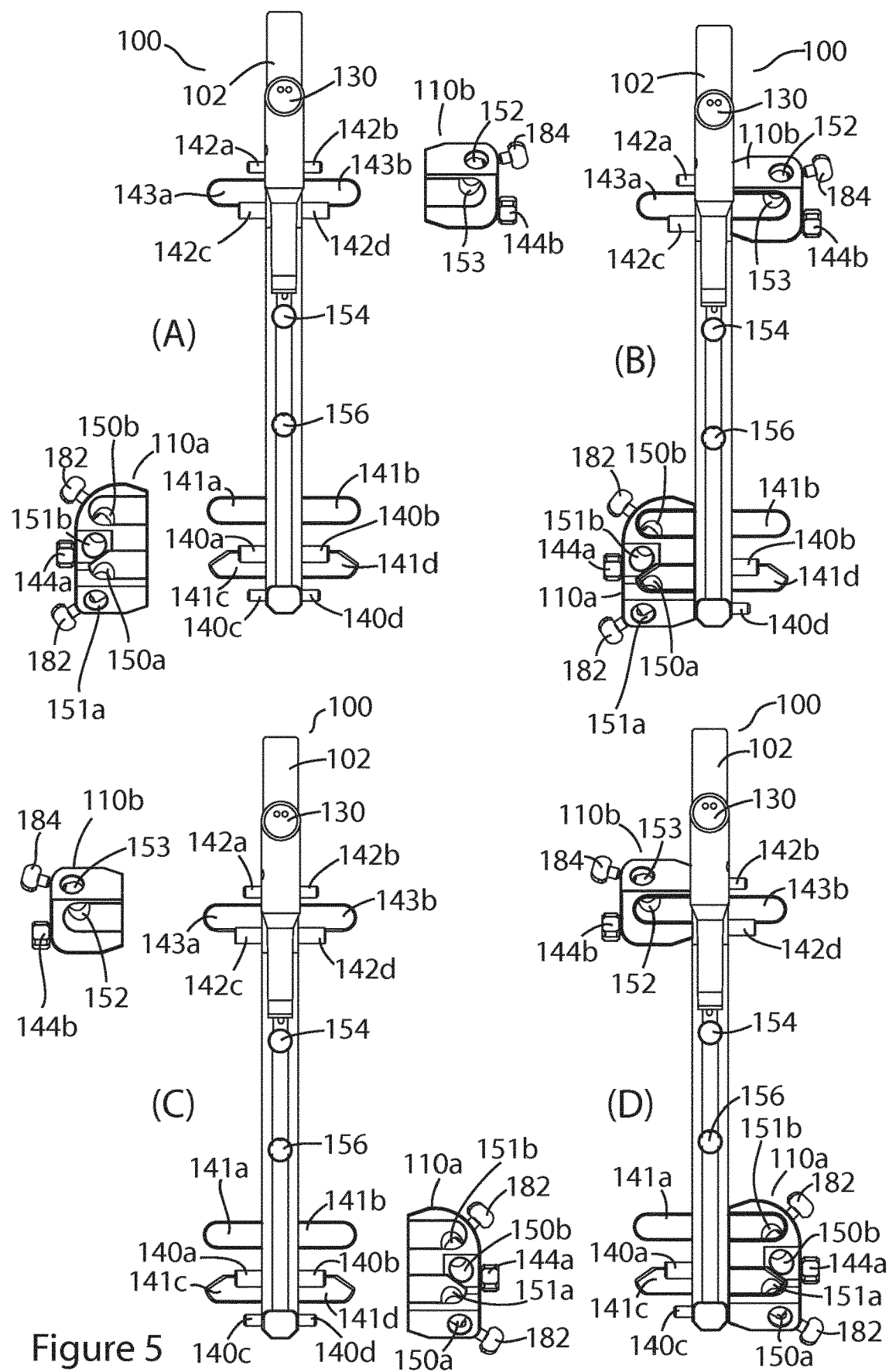
FIG. 5 illustrates, in FIGS. 5A-5D, the instrumentation of the present invention for use with a left/right leg inserted either antegrade or retrograde.
Figure 6:
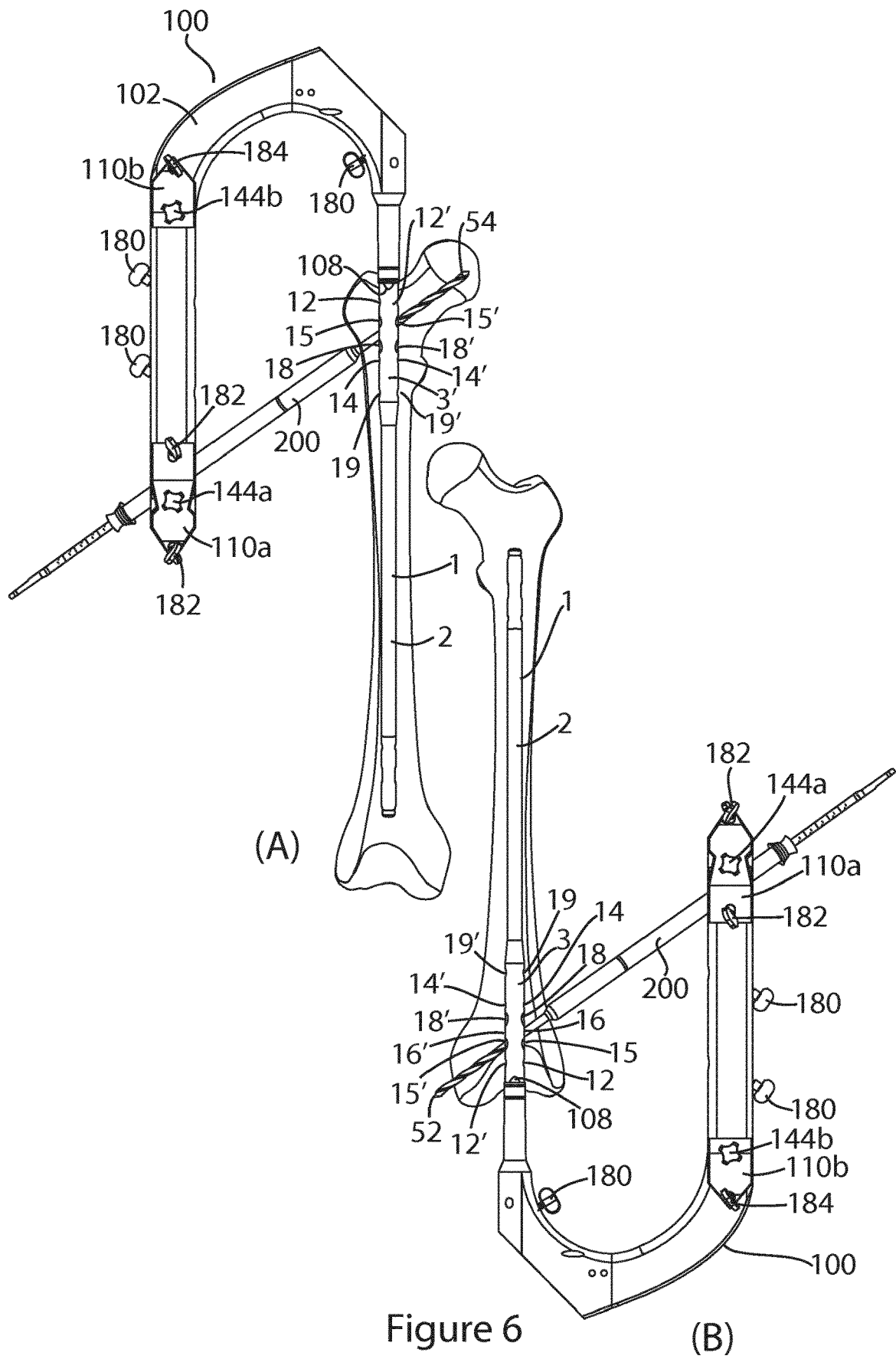
FIG. 6 illustrates the instrumentation and femoral intramedullary nail system of the invention being used from an antegrade (FIG. 6A) and a retrograde (FIG. 6B) implantation direction.

During the surgical procedure, a user can use an instrumentation system as illustrated in FIG. 3, which is given the reference numeral 100. The instrumentation system 100 is configured to cooperate with the IM nail system 1 described herein in order to implant the nail 2 and place the bone screws 50,52,54,56 in the desired trajectories. The fastener 4 is placed in the multi-featured proximal end 3 of the nail 2 with an alignment pin 6 in situ, ensuring the correct alignment of all apertures/holes of the nail 2 and fastener 4 prior to attaching to an instrumentation system 100. The fastener 4 comprises a proximal end 307 from which a raised foot 124 (see FIG. 4) extends vertically and parallel to a vertical axis of the fastener 4 and which is configured to matingly engage with an internal wall 3a of the proximal end 3 of the nail stem 2 to provide control over rotational and axial movement of the system 1 when secured with a bone screw. The instrumentation system 100 comprises a bone screw aiming arm 102, a connecting bolt 104 and a fastener camlock 106. The aiming arm 102 is attached to the proximal end 3 of the nail 2, rotation is controlled by a raised tooth 108 on the end of the aiming arm 102 that mates with a groove 160 (see FIG. 3D) in the proximal end 3 of the nail 2. The connection bolt 104 is inserted through a conduit 130 in aiming arm 102 and threads into the proximal end 3 of nail stem 2, fixing the nail stem 2 and aiming arm 102 together. The fastener camlock 106 is then placed through a conduit 134 of the connection bolt 104 until it stops against the top surface (proximal end 307) of the fastener 4. Rotation of the fastener camlock 106 then engages its end cam feature 116 on a raised foot 124 of the fastener 4 (see FIG. 4A/B), clamping the fastener 4 relative to the IM nail system 1 via a radial force. The alignment pin 6, configured to secure the fastener 4 during assembly of the fastener camlock 106 and connecting bolt 104 inside the conduit 130 of the aiming arm 102, is then removed, clearing a central passage 117 (see FIG. 4A) and readying the IM nail 2 for insertion. Fixation screws 180 are employed in the aiming arm 102 to clamp a drill sleeve 200 (see FIG. 6) during pilot hole drilling prior to fixing the bone.

FIG. 4A illustrates a longitudinal detailed view of the fastener camlock 106 engaged with the fastener 4. FIG. 4B illustrates a sectional view through the assembled system 1, specifically the fastener camlock 106 and fastener 4, to highlight the cam feature 116 engaged with the raised foot 124 of the fastener 4. The raised foot 124 of the fastener 4 extends laterally from the proximal end 7 relative to a vertical axis of the fastener 4

The instrumentation 100 further comprises modular blocks 110a,110b (see FIG. 5A-D). Depending on whether the desired implantation is antegrade-retrograde, right-left leg, the blocks 110a,110b are attached to the aiming arm 102. Block 110a is interchangeable and can be slid onto pins 140a,140c or 140b,140d on either side of aiming arm 102 and clamped in place with bolt 144a. Illustrations on aiming arm 102 and block 110a indicate which orientation to utilise for right or left leg. Once in position, wings 141a,141c or 141b,141d, cover over any aiming holes 150a,150b in the blocks 110a that are not required, with only aiming holes 151a,151b on the blocks 110a to match with the nail stem 2 and the fastener 4, allowing the placement of ascending bone screws on the nail stem 2. Block 110b is interchangeable to be slid onto pins 142a,142c or 142b,142d on either side of aiming arm 102, and clamped in place with bolt 144b. Illustrations on aiming arm 102 and block 110b indicate which orientation to utilise for right or left leg. Once placed, wings 143a,143b cover hole 153, which is not required, with only hole 152 open on the block 110b to match with the nail stem 2 and the fastener 4, allowing the placement of descending screws on the nail stem 2. Blocks 110a and 110b both include an opening to accepts drill sleeves and drills for pilot hole drilling before screw placement through the sleeve. Furthermore, mediolateral screw 50 can be placed via pilot hole drilling in opening 154 in aiming arm 102. An additional mediolateral screw can be placed distal to all screws in opening 156 in aiming arm 102. Fixation pins 182,184 are employed in block 110b and 110a, respectively, to clamp the drill sleeve 200 (see FIG. 6) during pilot hole drilling prior to fixing the bone.

The pins 142b,142d on the aiming arm 102 having wings 143b block redundant screw trajectory 153 when the modular block 110b is symmetric and attached to the aiming arm 102.

The pins 142a,142c on the aiming arm 102 having wings 143a block redundant screw trajectory 152 when the modular block 110b is symmetric and attached to the aiming arm 102.

The pins 140a,140c on the aiming arm 102 having wings 141a,141c block redundant screw trajectory 150a,150b and present screw trajectory 151a,151b when the modular block 110a is symmetric and attached to the aiming arm 102.

The pins 140b,140d on the aiming arm 102 having wings 141b,141d block redundant screw trajectory 151a,151b) and present screw trajectory 150a,150b when the modular block 110a is symmetric and attached to the aiming arm 102.

FIG. 6A and FIG. 6B illustrate the instrumentation system 100 and the femoral intramedullary nail system 1 being used from an antegrade and a retrograde implantation direction, respectively. With the nail system 1 in situ, and connected to the instrumentation system 100, the aiming arm 102 only presents the surgeon/user with the screw trajectories required for a particular orientation screw placement that has been preordained by the surgeon/user. As shown here, pilot drilling for bone screw 54 in antegrade (FIG. 6A) and retrograde (FIG. 6B) configurations are configured for insertion by the placement of the modular block 110b on the aiming arm 102. The positioning of the modular block 110b presents specific aiming holes 150a that means a specific trajectory is only available to the surgeon/user. Also using block 110b and opening 150b a pilot hole trajectory for a second screw 52 can be drilled. In the same manner pilot hole drilling can be completed through block 110a and aiming hole 150b for descending screws 56.

One of the advantages of the instrumentation system 100 is that when the fastener camlock 106 is assembled into the connecting bolt 104, the camlock 106 clamps onto the fastener 4 proximal end (see FIGS. 3B and 4) and applies the clamping force in the radial direction. This removes any applied force on the alignment pin 6, allowing its easy removal.

Another advantage is that the alignment arm 102 that presents only the desired bone screw hole trajectories for bone screw placement. When a combined right/left leg antegrade/retrograde product (see FIG. 6A and FIG. 6B) is being implanted, conventional targeting arms present all possible screw locations simultaneously. This can result in a surgeon attempting to place or placing a screw in an incorrect location. With the adoption of modular blocks 110a, 110b that are reversible for right versus left screw/nail implantation, and the addition of a blinding feature for those holes not to be used (the wings 141a,141b,141c,141d,143a, 143b), the aiming arm 102 only presents the surgeon/user with the screw trajectories required for that particular orientation screw placement.

A further advantage of the claimed invention is that the instrumentation 100 and the nail system 1 can place four laterally inserted bone screws 50,52,54,56 (including a horizontal medio-lateral screw distal to the other three screws) antegrade into a femoral neck in the shortest axial length to fit the patient anatomy. By matching the patient anatomy, the bone screws 50,52,54,56 will not break out through the base of the neck in the femur or out the top, which is an issue with the systems of the prior art. The arrangement of the systems 1 and 100 permit having three bone screws 50,52,54,56 in one direction, i.e. antegrade placement lateral to medial, ascending and horizontal for a right or left leg. The three laterally inserted bone screws 50,52,54,56 that are placed in the femoral head provide multi-planar fixation, as the bone screws 50,52,54,56 are in an-off angle configuration when viewed on axis, and spreads the load on the distal end of the bone screws 50,52,54,56, which improves the fixation in poor quality bone and reduces the potential for the bone screw to pull out. This off-angle bone screw placement reduces the likelihood of femoral head rotation relative to the femur.

In the specification, the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. An intramedullary femoral nail system (1) for antegrade or retrograde implantation with laterally inserted bone screws, the system comprising a nail stem (2) having a multi-featured proximal end (3), a distal end and a central conduit (22); and a fastener (4), wherein the central conduit is configured to accommodate the fastener (4), wherein the multi-featured proximal end (3) comprises a plurality of holes (12,12',14,14',15,15',16,16',18,18',19,19'), which align with a plurality of corresponding holes in the fastener (4), configured to accommodate at least three laterally inserted bone screws (50,52,54,56), wherein the first hole (12) configured to accommodate the first bone screw (50) is at an angle that is horizontal relative to the central conduit (22) and is on a coronal plane, the hole (14) configured to accommodate the second bone screw (52) is at an angle of between about 120° to about 124° relative to the central conduit (22), and the hole (16) configured to accommodate the third bone screw (54) is at an angle of 123° relative to the central conduit (22), and wherein the second and third bone screws (52,54) accommodated within the holes (14 and 16) are not parallel to each other.

2. The intramedullary femoral nail system (1) for antegrade or retrograde implantation with laterally inserted bone screws according to claim 1, wherein the hole (14) configured to accommodate the second bone screw (52) is at an angle of 123° relative to the central conduit (22) and in an ascending approach relative to the hole (12) configured to accommodate the first bone screw (50).

3. The intramedullary femoral nail system (1) according to claim 1, wherein the holes (14,16) configured to accommodate the second and third bone screw (52,54) are rotated at an angle of at least 14° in an anterior direction relative to the coronal plane.

4. The intramedullary femoral nail system (1) according to claim 1, wherein the hole (18) configured to accommodate a fourth bone screw (56) is at an angle of 123° relative to the central conduit (22) and in a descending approach relative to the holes (12,14) configured to accommodate the first bone screw (50) and the second bone screw (52).

5. The intramedullary femoral nail system (1) according to claim 1, wherein there is a medio lateral hole (19) configured to accommodate a fifth bone screw that is placed distal to all other bone screws (50,52,54,56).

6. The intramedullary femoral nail system (1) according to claim 1, further comprising an end cap adapted to matingly engage with a threaded portion (26) of the proximal end (3) of the nail stem (2).

7. An instrumentation system (100) for antegrade or retrograde implantation with laterally inserted screws for use with an intramedullary femoral nail system (1), the intramedullary femoral nail system (1) comprising a nail stem (2) having a multi-featured proximal end (3), a distal end and a central conduit (22); and a fastener (4), wherein the central conduit is configured to accommodate the fastener (4); wherein the multi-featured proximal end (3) comprises a plurality of holes (12,12',14,14',15,15',16,16', 18,18',19,19'), which align with a plurality of corresponding holes in the fastener (4), configured to accommodate at least three laterally inserted bone screws (50,52,54,56), wherein the first hole (12) configured to accommodate the first bone screw (50) is at an angle that is horizontal relative to the central conduit (22) and is on a coronal plane, the hole (14) configured to accommodate the second bone screw (52) is at an angle of between about 120° to about 124° relative to the central conduit (22), and the hole (16) configured to accommodate the third bone screw (54) is at an angle of 123° relative to the central conduit (22), and wherein the second and third bone screws (52,54) accommodated within the holes (14 and 16) are not parallel to each other; and wherein the instrumentation system (100) comprises an aiming arm (102), a cannulated connecting bolt (104) comprising a threaded portion that is configured to matingly engage with a nail stem (2) of the nail system (1), the fastener (4) configured to engage with the nail system (1), and a fastener camlock (106) comprising an end cam feature (116) configured to matingly engage with the fastener (4) and the cannulated connection bolt (104); wherein the fastener camlock (106) further comprises a shaft section (117) to engage the cannulated connecting bolt (104), and a distal head (118).

8. An instrumentation system (100) for antegrade or retrograde implantation with laterally inserted screws for use with an intramedullary femoral nail system (1) for antegrade or retrograde implantation with laterally inserted bone screws, the intramedullary femoral nail system comprising a nail stem (2) having a multi-featured proximal end (3), a distal end and a central conduit (22); and a fastener (4), wherein the central conduit is configured to accommodate the fastener (4); wherein the multi-featured proximal end (3) comprises a plurality of holes (12,12',14,14',15,15',16,16', 18,18',19,19'), which align with a plurality of corresponding holes in the fastener (4), configured to accommodate at least three laterally inserted bone screws (50,52,54,56), wherein the first hole (12) configured to accommodate the first bone screw (50) is at an angle that is horizontal relative to the central conduit (22) and is on a coronal plane, the hole (14) configured to accommodate the second bone screw (52) is at an angle of between about 120° to about 124° relative to the central conduit (22), and the hole (16) configured to accommodate the third bone screw (54) is at an angle of 123° relative to the central conduit (22), and wherein the second and third bone screws (52,54) accommodated within the holes (14 and 16) are not parallel to each other, wherein the instrumentation system (100) comprises an aiming arm (102), a cannulated connecting bolt (104) comprising a threaded portion that is configured to matingly engage with a nail stem (2) of the nail system (1), a fastener (4) configured to engage with the nail system (1), further comprising a modular block (110a,110b) configured to attach to the aiming arm (102) to consistently provide lateral bone screw trajectories for either a right or a left antegrade or retrograde implantation.

9. The instrumentation system (100) and the intramedullary nail system (1) according to claim 8 in which when the modular block (110a,110b) is attached to the aiming arm (102) via pins (140a-d,142a-d) on the aiming arm (102), the modular block (110a,110b) presents screw trajectories (150a, 150b, 151a, 150b, 152, 153) on block (110a, 110b) for inserting the bone screws (50,52,54,56).

10. The instrumentation system (100) for antegrade or retrograde implantation with laterally inserted screws for use with an intramedullary femoral nail system (1) for antegrade or retrograde implantation with laterally inserted bone screws of claim 8, further comprising: a fastener camlock (106) comprising an end cam feature (116) configured to matingly engage with the fastener (4) and the cannulated connection bolt (104).

11. The instrumentation system (100) for antegrade or retrograde implantation with laterally inserted screws for use with an intramedullary femoral nail system (1) for antegrade or retrograde implantation with laterally inserted bone screws of claim 10, wherein a hole (18) configured to accommodate a fourth bone screw (56) is at an angle of 123° relative to the central conduit (22) and in a descending approach relative to the holes (12,14) configured to accommodate the first bone screw (50) and the second bone screw (52).

12. The instrumentation system (100) for antegrade or retrograde implantation with laterally inserted screws for use with an intramedullary femoral nail system (1) for antegrade or retrograde implantation with laterally inserted bone screws of claim 11, further comprising a medio lateral hole (19) configured to accommodate a fifth bone screw that is placed distal to all other bone screws (50,52,54,56).

13. The instrumentation system (100) for antegrade or retrograde implantation with laterally inserted screws for use with an intramedullary femoral nail system (1) for antegrade or retrograde implantation with laterally inserted bone screws of claim 12, further comprising an end cap adapted to matingly engage with a threaded portion (26) of the proximal end (3) of the nail stem (2).

14. An instrumentation system (100) and an intramedullary femoral nail system (1) for antegrade or retrograde implantation with laterally inserted bone screws, wherein the instrumentation system (100) comprises an aiming arm (102), a cannulated connecting bolt (104) comprising a threaded portion that is configured to matingly engage with a nail stem (2) of the nail system (1), a fastener (4) thereof configured to engage with the nail system (1); wherein the intramedullary femoral nail system (1) comprises a nail stem (2) having a multi-featured proximal end (3), a distal end and a central conduit (22) configured to accommodate the fastener (4), wherein the multi-featured proximal end (3) comprises a plurality of holes (12,12',14,14',15,15',16,16', 18,18',19,19'), which align with a plurality of corresponding holes in the fastener (4), configured to accommodate at least three laterally inserted bone screws (50,52,54,56), wherein the first hole (12) configured to accommodate the first bone screw (50) is at an angle that is horizontal relative to the central conduit (22) and is on a coronal plane, the hole (14) configured to accommodate the second bone screw (52) is at an angle of between about 120° to about 124° relative to the central conduit (22), and the hole (16) configured to accommodate the third bone screw (54) is at an angle of 123° relative to the central conduit (22), and wherein the second and third bone screws (52,54) are accommodated within the holes (14,16) are not parallel to each other.

15. The instrumentation system (100) and an intramedullary femoral nail system (1) for antegrade or retrograde implantation with laterally inserted bone screws of claim 14, further comprising: a fastener cam lock (106) comprising an end cam feature (116) configured to matingly engage with the fastener (4) and the cannulated connection bolt (104).

16. The instrumentation system (100) and an intramedullary femoral nail system (1) for antegrade or retrograde implantation with laterally inserted bone screws of claim 15, further comprising: a modular block (110a,110b) configured to attach to the aiming arm (102) to consistently provide lateral bone screw trajectories for either a right or a left antegrade or retrograde implantation.

17. The instrumentation system (100) and an intramedullary femoral nail system (1) for antegrade or retrograde implantation with laterally inserted bone screws of claim 16, further comprising: when the modular block (110a,110b) is attached to the aiming arm (102) via pins (140a-d,142a-d) on the aiming arm (102), the modular block (110a,110b) presents screw trajectories (150a, 150b, 151a, 150b, 152, 153) on block (110a, 110b) for inserting the bone screws (50,52,54,56).

18. The instrumentation system (100) and an intramedullary femoral nail system (1) for antegrade or retrograde implantation with laterally inserted bone screws of claim 17, wherein the holes (14,16) configured to accommodate the second and third bone screw (52,54) are rotated at an angle of at least 14° in an anterior direction relative to the coronal plane.

19. The instrumentation system (100) and an intramedullary femoral nail system (1) for antegrade or retrograde implantation with laterally inserted bone screws of claim 18, wherein a hole (18) configured to accommodate a fourth bone screw (56) is at an angle of 123° relative to the central conduit (22) and in a descending approach relative to the holes (12,14) configured to accommodate the first bone screw (50) and the second bone screw (52).

20. The instrumentation system (100) and an intramedullary femoral nail system (1) for antegrade or retrograde implantation with laterally inserted bone screws of claim 19, further comprising a medio lateral hole (19) configured to accommodate a fifth bone screw that is placed distal to all other bone screws (50,52,54,56).

* * * * *